US010369322B2

United States Patent
Feil et al.

(10) Patent No.: US 10,369,322 B2
(45) Date of Patent: Aug. 6, 2019

(54) RESPIRATOR

(71) Applicant: Dräger Safety AG & Co. KGaA, Lübeck (DE)

(72) Inventors: Dirk Feil, Lübeck (DE); Alexander Busch, Lübeck (DE); Volker Nesch, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 953 days.

(21) Appl. No.: 14/423,193

(22) PCT Filed: Aug. 9, 2013

(86) PCT No.: PCT/EP2013/066683
§ 371 (c)(1),
(2) Date: Feb. 23, 2015

(87) PCT Pub. No.: WO2014/029637
PCT Pub. Date: Feb. 27, 2014

(65) Prior Publication Data
US 2015/0250977 A1    Sep. 10, 2015

(30) Foreign Application Priority Data
Aug. 21, 2012  (DE) .................. 10 2012 214 860

(51) Int. Cl.
*A61M 16/06*    (2006.01)
*A61M 16/20*    (2006.01)
(Continued)

(52) U.S. Cl.
CPC ...... *A61M 16/205* (2014.02); *A61M 16/0003* (2014.02); *A61M 16/0063* (2014.02);
(Continued)

(58) Field of Classification Search
CPC ........ A61M 16/00; A61M 16/06–0694; A61M 16/20–209; A61M 16/003–0012;
(Continued)

(56) References Cited

U.S. PATENT DOCUMENTS

| 3,859,995 A * | 1/1975 | Colston ................. B63C 11/24 128/204.25 |
| 3,957,044 A * | 5/1976 | Fletcher ................. A62B 7/04 128/202.22 |
| 2005/0051169 A1 * | 3/2005 | Gossweiler ............. A62B 9/02 128/205.24 |
| 2006/0048777 A1 | 3/2006 | Brookman |

(Continued)

FOREIGN PATENT DOCUMENTS

| CN | 101001672 A | 7/2007 |
| CN | 101426555 A | 5/2009 |

(Continued)

*Primary Examiner* — Tan-Uyen T Ho
*Assistant Examiner* — Ned T Heffner
(74) *Attorney, Agent, or Firm* — McGlew and Tuttle, P.C.

(57) ABSTRACT

A breathing apparatus includes a compressed air source with a compressed air source valve, a breathing regulator with a pressure reducer and a demand valve, a breathing mask connected to the demand valve at a first inlet connector, a second air source, a switching mechanism having an actuating member for switching between the compressed air source and the second air source and an exhalation valve, on the breathing mask, movable between a higher internal pressure in a second operating state than in a first operating state. The actuating member is provided on the breathing regulator. The switching mechanism, upon being switching to compressed air breathing, activates the lung-governed demand valve and adjusts the exhalation valve to the second operating state. Upon switching to breathing via the second (Continued)

air source, the lung-governed demand valve is deactivated and the exhalation valve (30) is adjusted to the first operating state.

16 Claims, 4 Drawing Sheets

(51) Int. Cl.
  *A62B 7/02* (2006.01)
  *A62B 18/10* (2006.01)
  *A61M 16/00* (2006.01)
  *A61M 16/08* (2006.01)
(52) U.S. Cl.
  CPC ........ *A61M 16/06* (2013.01); *A61M 16/0816* (2013.01); *A62B 7/02* (2013.01); *A62B 18/10* (2013.01); *A61M 2016/0027* (2013.01); *A61M 2205/3331* (2013.01)
(58) Field of Classification Search
  CPC ... A61M 2016/0015–0042; A62B 9/00; A62B 9/02–027; A61B 18/00; A61B 18/10; B63C 11/12; B63C 11/18
  See application file for complete search history.

(56) References Cited

U.S. PATENT DOCUMENTS

| | | | |
|---|---|---|---|
| 2007/0251525 A1* | 11/2007 | Prete | A62B 9/02 128/204.18 |
| 2010/0236554 A1 | 9/2010 | Prete | |
| 2011/0209712 A1 | 9/2011 | Busch et al. | |

FOREIGN PATENT DOCUMENTS

| | | |
|---|---|---|
| EP | 2 361 656 A1 | 8/2011 |
| GB | 2 264 646 A | 9/1993 |
| WO | 2006012475 A2 | 2/2006 |
| WO | 2007/123585 A1 | 11/2007 |
| WO | 2013/103343 A1 | 7/2013 |

* cited by examiner

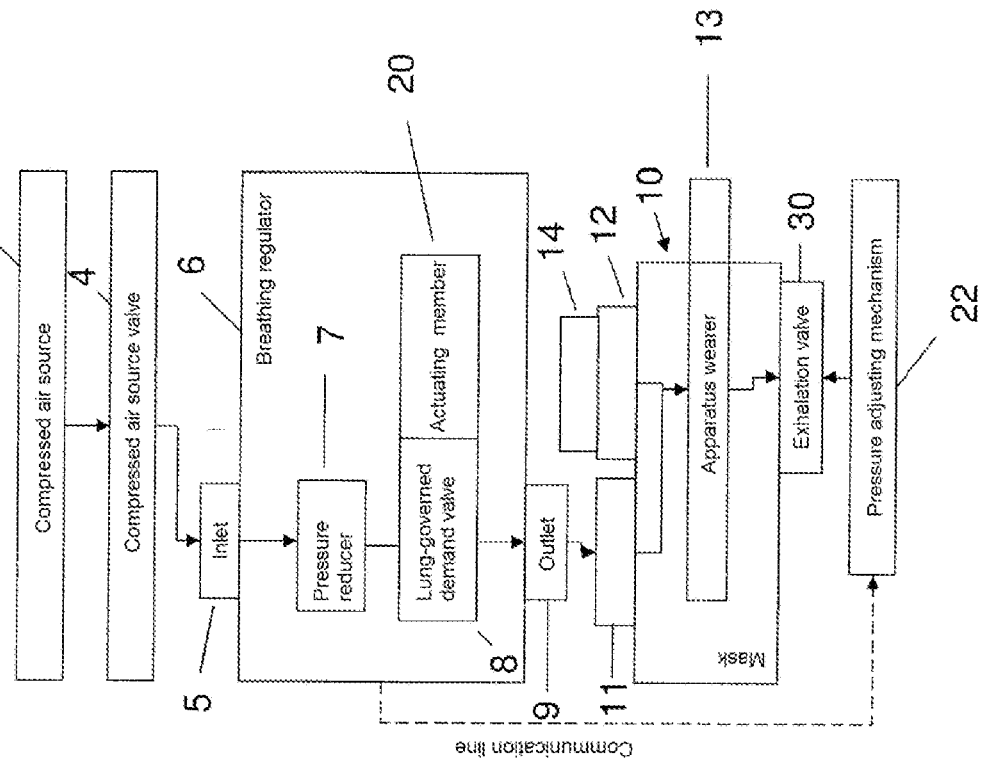
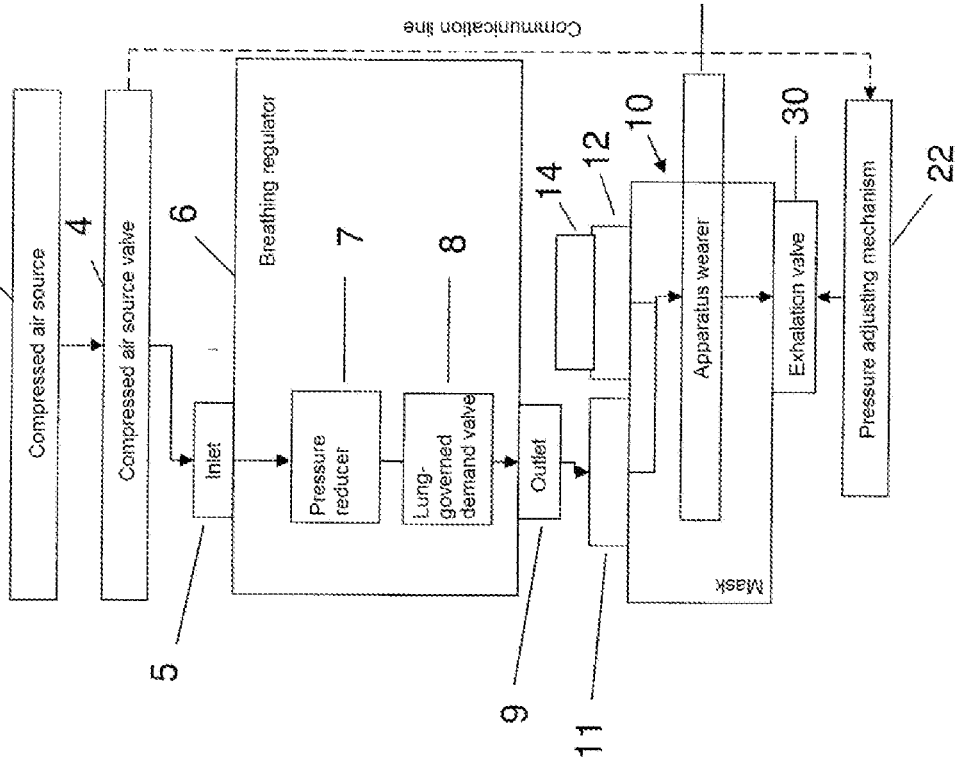

RESPIRATOR

CROSS REFERENCE TO RELATED APPLICATIONS

This application is a United States National Phase Application of International Application PCT/EP2013/066683 filed Aug. 9, 2013 and claims the benefit of priority under 35 U.S.C. § 119 of German Patent Application DE 10 2012 214 860.4 filed Aug. 21, 2012, the entire contents of which are incorporated herein by reference.

FIELD OF THE INVENTION

The present invention relates to a breathing apparatus having a compressed air source with a compressed air source valve, a breathing regulator which is connected to the compressed air source valve and has a pressure reducer and a lung-governed demand valve, a breathing mask which is attached to the lung-governed demand valve (directly or via a hose), a second air source which is connected either to a second inlet connector of the breathing mask or to a connector with direct connection to the lung-governed demand valve, a switching mechanism having an actuating member, operation of which effects switching between compressed air breathing from the compressed air source via the lung-governed demand valve and breathing from the second air source, an exhalation valve on the breathing mask, which valve is movable between a first and a second operating state, a higher internal pressure being effected in the breathing mask in the second operating state than in the first operating state. The invention relates to a breathing unit comprising a breathing mask and a breathing regulator, which can be used in the breathing apparatus of the invention.

BACKGROUND OF THE INVENTION

Breathing apparatuses have breathing masks to which different air sources can be attached: filter, power-assisted filtering device, compressed air breathing apparatus. The combination of breathing mask and air source yields breathing apparatuses which are referred to as follows in U.S. American parlance:
  air purifying respirator (APR): breathing mask+filter
  powered air purifying respirator (PAPR): breathing mask+power-assisted filtering device
  self-contained breathing apparatus (SCBA): breathing mask+compressed air breathing apparatus.

These breathing apparatuses differ for the user primarily by the protection factor that is provided. The breathing masks are tailored to the apparatus that it is to be attached to, a mask for filter use is accordingly not the same in terms of construction as a mask for use for compressed air breathing. There are apparatuses that are self-contained: that is to say, it is generally not possible to attach a filter to a compressed air breathing mask. Because a compressed air breathing apparatus exists as a normal pressure and an overpressure (positive pressure) variant, a further differentiation between mask types is necessary in this case: normal pressure masks and overpressure masks. In the case of the latter, the exhalation valve is biased with a spring force in order to achieve a static overpressure in the mask. This increases the protection factor, because a positive pressure gradient is thus maintained from the inside to the outside.

Some use scenarios require the use of different types of breathing apparatus. So-called hybrid masks offer the possibility of selectably using one of two of the breathing apparatuses mentioned at the beginning in one breathing apparatus. The combinations APR/SCBA or PAPR/SCBA are common. The compressed air breathing apparatus is thereby generally in the form of an overpressure system, the other two apparatus types are, by definition, normal pressure systems. For the breathing mask, it is thereby necessary to be able to change the exhalation valve from a normal pressure state into an overpressure state and vice versa. In the case of such hybrid apparatuses, it is necessary to disconnect one air source (e.g. compressed air breathing apparatus) and connect another air source (e.g. filter—filtered ambient air).

U.S. 2007/0251525 A1 discloses a known breathing apparatus which can be switched from an operating state in which ambient air drawn in through a filter serves as the air source, to an operating state in which the breathing apparatus is supplied by a compressed air breathing apparatus, and vice versa. The operating state of the breathing apparatus is determined by the switch position of the compressed air cylinder valve (open or closed). The known breathing apparatus has a compressed air source (e.g. compressed air cylinder) with a compressed air source valve. This compressed air source valve is referred to as an actuator and has two functions in the known breathing apparatus:
1. opening the valve leads to the flow of compressed air and thus places the pneumatic system of the breathing apparatus under pressure, closing the valve closes the compressed air source and thus prevents the flow of compressed air;
2. in addition to the mentioned pressure rise in the pneumatic system of the breathing apparatus, opening the valve leads to activation of a pressure adjusting mechanism and thus to switching of the exhalation valve from the first operating state into the second operating state.

According to the description of the known breathing apparatus, there is a communicative link between the compressed air source valve and the exhalation valve. It is mentioned that information about the opening or closing of the valve can be transmitted in different ways, in particular pneumatically, electrically, hydraulically, mechanically, etc., via the communicative link. If the communication path performs pneumatic transmission of information, opening of the compressed air cylinder valve on the one hand causes the pneumatic system of the breathing apparatus to be placed under pressure and on the other hand causes the exhalation valve to be moved into the second operating state, in which a higher internal pressure is built up in the breathing mask.

Such a configuration of a breathing apparatus has the advantage that, by operation of a single actuating member (compressed air cylinder valve), both the compressed air cylinder valve is opened and the exhalation valve is moved into the second operating state, so that a higher internal pressure is built up in the breathing mask. On the other hand, this has the disadvantage that the pneumatic system of the breathing apparatus is not placed under pressure until switching to compressed air breathing is actually to be carried out. This is then effected only in a situation in which the wearer of the breathing apparatus is moving in an increasingly more hazardous environment, when the wearer wishes to change from breathing via the filter to compressed air breathing. This has the disadvantage that a fault in the build-up of pressure in the pneumatic system of the breathing apparatus caused by any type of malfunction downstream of the compressed air source valve does not manifest itself as incomplete or failed build-up of pressure in the pneumatic system of the breathing apparatus until the time when compressed air breathing is actually required.

SUMMARY OF THE INVENTION

It is therefore desirable to provide a breathing apparatus which is simpler to handle and more reliable.

According to the invention, a breathing apparatus is provided comprising a compressed air source with a compressed air source valve, a breathing regulator connected to the compressed air source valve, the breathing regulator comprising a pressure reducer and a lung-governed demand valve, a breathing mask comprising a first inlet connector operatively connected to the lung-governed demand valve and a second inlet connector, a second air source operatively connected to the second inlet connector of the breathing mask or to a connector with direct connection to the lung-governed demand valve, a switching mechanism, with an actuating member effecting switching between compressed air breathing from the compressed air source via the lung-governed demand valve and breathing from the second air source and an exhalation valve on the breathing mask. The exhalation valve is movable between a first and a second operating state. A higher internal pressure being effected in the breathing mask in the second operating state than in the first operating state.

According to an aspect the actuating member of the switching mechanism is provided on the breathing regulator, the switching mechanism being so configured that, upon switching to compressed air breathing, the switching mechanism activates the lung-governed demand valve (lung demand valve (LDV)) and adjusts the exhalation valve to the second operating state and, upon switching to breathing via the second air source, the switching mechanism deactivates the lung-governed demand valve and adjusts the exhalation valve to the first operating state. In the active state, the lung-governed demand valve delivers compressed air at the first inlet connector of the breathing mask; in the deactivated state, it is blocked (or closed) and does not supply compressed air to the breathing mask, even if compressed air is present at the outlet of the pressure reducer.

Such a breathing apparatus is more simple and more reliable to handle for the wearer of the breathing apparatus, referred to in the following as the apparatus wearer, in practical application. In practical application, the apparatus wearer fits the breathing apparatus in a non-hazardous environment even before it is actually in use. The apparatus wearer then opens the compressed air source valve, which is still easily possible in the non-hazardous environment before the apparatus is actually in use, even if the compressed air source valve is located, for example, on a compressed air cylinder behind the back of the apparatus wearer and is scarcely visible to the apparatus wearer, so that it is necessary to feel for it. In the case of the known breathing apparatus described at the beginning, this opening of the compressed air source valve, which can be difficult in critical situations, does not take place until the apparatus is in use under hazardous environmental conditions, when switching from breathing via the filter to compressed air breathing is to be carried out. With the configuration according to the invention of the breathing apparatus, this opening of the compressed air source valve can take place in a stress-free situation before the apparatus is actually in use.

A further advantage of the breathing apparatus according to embodiments of the invention is that the build-up of pressure in the breathing apparatus after opening of the compressed air source valve to the lung-governed demand valve takes place in the non-critical situation before the apparatus is in use, when the apparatus wearer opens the compressed air source valve before use. It is then possible to check, in that stress-free and non-critical situation, that the build-up of pressure after opening the compressed air source valve in the breathing apparatus to the lung-governed demand valve actually takes place without problems. Should a malfunction which impairs the build-up of pressure in the breathing apparatus occur downstream of the compressed air source valve and upstream of the lung-governed demand valve, such a defect would manifest itself with the breathing apparatus according to the invention in the non-critical situation before use—or in use but during the phase of slight respiratory protection and accordingly in a less hazardous ambient atmosphere—when the compressed air source valve is opened. The apparatus wearer could then replace the breathing apparatus or ensure that the malfunction is eliminated before the apparatus is actually used or, if the fault occurs in use, the apparatus wearer could stop using the apparatus before a profoundly hazardous ambient atmosphere is reached. If the build-up of pressure after opening of the compressed air source valve has taken place correctly, the apparatus wearer of the breathing apparatus can start to use the compressed air source, breathing initially taking place via a second air source, for example with a filter on the breathing mask. When the apparatus wearer of the breathing apparatus then approaches a region in which the atmospheric conditions worsen and breathing is to be switched to compressed air breathing, the wearer simply operates the actuating member of the switching mechanism on the breathing regulator, as a result of which the lung-governed demand valve is activated and the exhalation valve is moved into the second operating state with higher pressure in the breathing mask. This initiation of compressed air breathing by manual operation on the breathing regulator, which is located in the region in front of the mouth within sight of the apparatus wearer of the breathing apparatus, is substantially simpler than the initiation of compressed air breathing by opening the compressed air source valve behind the back of the apparatus wearer. Therefore, switching to compressed air breathing can take place by a more simple manual operation, which permits more reliable handling of the breathing apparatus in particular under critical and high-stress conditions during use.

In one embodiment, the switching mechanism has an actuating member on the lung-governed demand valve, which actuating member is configured to end valve blocking in the lung-governed demand valve when operated, and a pressure adjusting mechanism, which is configured to record the rise in pressure as a result of the ending of valve blocking and then to cause the exhalation valve to be switched into the second operating state. On reverse operation of the switch on the lung-governed demand valve, valve blocking in the lung-governed demand valve is closed again and the pressure adjusting mechanism records the associated pressure drop, whereupon the pressure adjusting mechanism causes the exhalation valve to be switched into the first operating state.

The pressure adjusting mechanism comprises, for example, a pneumatic spring-loaded valve, the piston of which is connected mechanically at one end to the exhalation valve for switching thereof between the first and the second operating state and vice versa. The opposite end of the piston is pneumatically exposed to the pressure of the breathing regulator. Furthermore, a spring force acting on the piston against the pneumatic force is additionally present, which spring force, in the pressureless (zero pressure)

state, causes a piston position of the pneumatic spring-loaded valve which effects a positioning of the exhalation valve in the normal pressure state. By activating the actuating member of the switching mechanism on the breathing regulator, the spring force acting on one side is exceeded by an increased pneumatic force which is in this case caused by the increased pressure, so that a change of the position of the piston of the pneumatic spring-loaded valve switches the exhalation valve into the second state by mechanical action thereon. In principle, however, many other configurations of the pressure adjusting mechanism can be provided; for example, the increased pressure after activation of the lung-governed demand valve could be detected by a pressure sensor which is connected to an actuator acting on the exhalation valve; if the pressure sensor does not record increased pressure, the actuator causes the exhalation valve to be in the first operating state, whereas if an increased pressure is recorded by the pressure sensor, the actuator is activated to effect the repositioning of the exhalation valve into the second operating state.

In another embodiment, the switching mechanism is realized in that the housing of the lung-governed demand valve is suspended (mounted) on the breathing mask in a linearly displaceable manner between a first and a second position, displacement from the first position into the second position ending internal valve blocking in the lung-governed demand valve and switching the exhalation valve from the first operating state into the second operating state and, conversely, displacement from the second position into the first position effecting valve blocking in the lung-governed demand valve and switching the exhalation valve from the second operating state into the first operating state. In this embodiment, the apparatus wearer can effect switching to compressed air breathing operation in a simple manner by pressing the lung-governed demand valve against the mask, whereby it is brought from the first position into the second position. The movement of the housing of the lung-governed demand valve from the first position into the second position can, for example, be transmitted mechanically to a lever, which is thereby pivoted. The lever abuts a spring, which presses with its other end on the exhalation valve. Pivoting of the lever causes the spring to be pressed more strongly against the exhalation valve, as a result of which the opening pressure of the valve is increased and the transfer from the first operating state into the second operating state is thereby effected. Conversely, when the housing of the lung-governed demand valve is withdrawn, it is brought from the second position into the first position, as a result of which the lever pivots back again so that the pressure of the spring on the exhalation valve is reduced and the exhalation valve is thereby moved into the first operating state. Activation of the lung-governed demand valve by moving the housing of the lung-governed demand valve can be effected, for example, by a pin which is fixed relative to the housing of the lung-governed demand valve and is so arranged that, upon displacement of the housing of the lung-governed demand valve from the first position into the second position, a valve of the lung-governed demand valve is pressed against the fixed pin, as a result of which the valve is opened and the lung-governed demand valve is thus released. Conversely, displacement of the housing of the lung-governed demand valve from the second position into the first position has the result that the fixed pin no longer presses against the valve of the lung-governed demand valve, as a result of which the valve is moved into its closed position without pressure of the pin, so that the lung-governed demand valve is deactivated or blocked.

In an embodiment, the switching mechanism has as the actuating member a manually operable valve which is arranged in the breathing regulator between the pressure reducer and the lung-governed demand valve, in order to open or close the flow of compressed air to the lung-governed demand valve by operation of the valve, and a pressure adjusting mechanism which is configured to record the rise in pressure as a result of the opening of the compressed air flow to the lung-governed demand valve and then cause the exhalation valve to be switched into the second operating state, and to record the pressure drop as a result of the closing of the compressed air flow to the lung-governed demand valve and then cause the exhalation valve to be switched into the first operating state.

According to a further aspect of the invention there is provided a breathing unit having a breathing regulator and a breathing mask. The breathing regulator, which has a pressure reducer and a lung-governed demand valve, can be connected to a compressed air source valve of a compressed air source. The breathing mask is connected at a first inlet connector to the lung-governed demand valve directly or via a hose and has a second inlet connector to which a second air source can be attached. There is further present a switching mechanism having an actuating member for switching between compressed air breathing from the compressed air source via the lung-governed demand valve or from the second air source. The breathing mask has an exhalation valve which can be moved between a first and a second operating state, a higher internal pressure being effected in the breathing mask in the second operating state than in the first operating state. This is achieved as a result of the fact that the exhalation valve has a higher flow resistance in the second operating state, so that the pressure in the inside of the mask increases. According to the invention, it is provided that the actuating member of the switching mechanism is arranged on the breathing regulator. The switching mechanism is so configured that, upon switching to compressed air breathing, it activates the lung-governed demand valve and adjusts the exhalation valve to the second operating state and, upon switching to breathing via the second air source by operation of the actuating member, it deactivates the lung-governed demand valve and adjusts the exhalation valve to the first operating state.

Embodiments of the invention will be described in greater detail in the following with reference to the drawings. The present invention shall be explained in more detail on the basis of the following figures and exemplary embodiments, without the present invention being limited to these. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 1 is a schematic view showing the construction of a breathing apparatus according to an embodiment of the invention;

FIG. 5 is a schematic view showing the construction of a breathing apparatus according to the prior art cited in the introduction.

DESCRIPTION OF THE PREFERRED EMBODIMENTS

Figure 2:
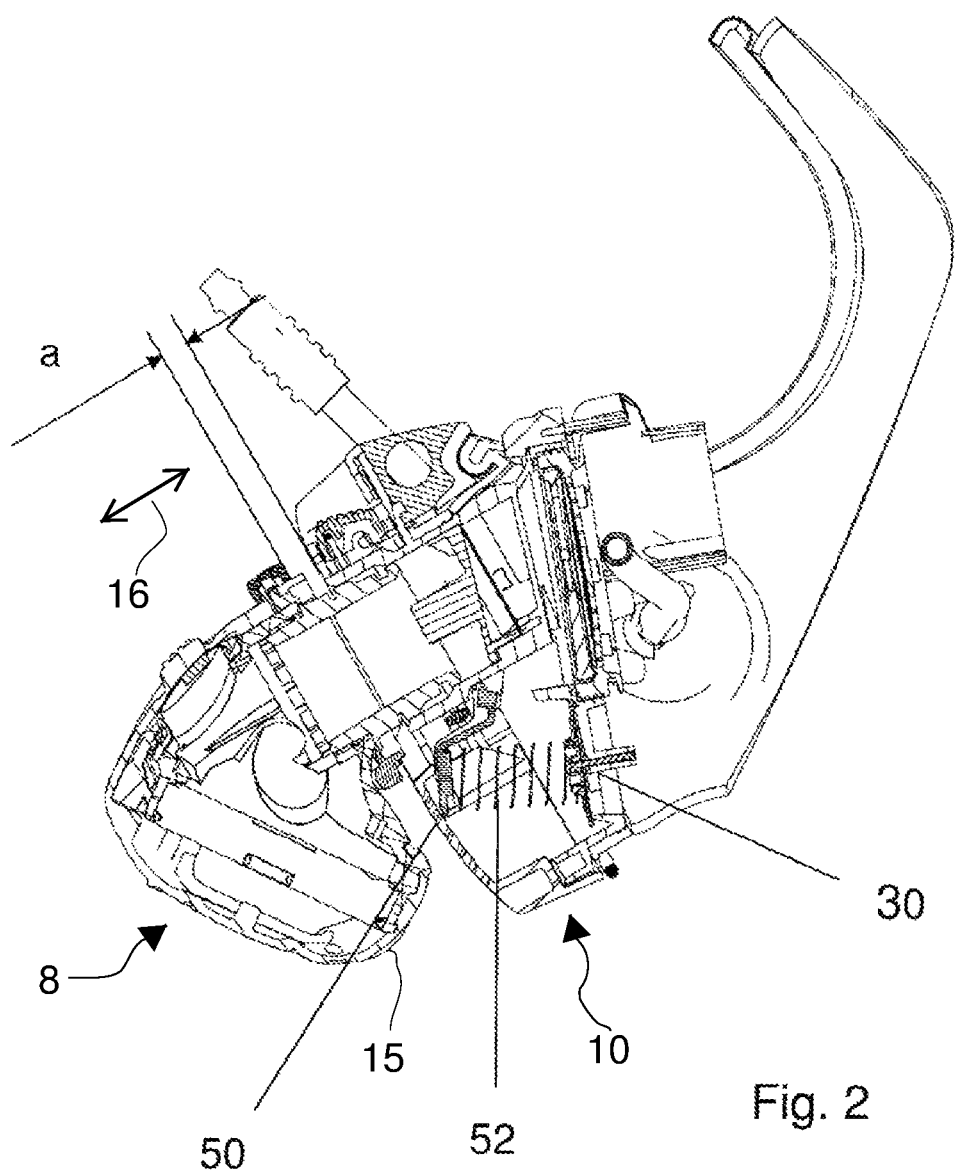
FIG. 2 is a sectional view of a lung-governed demand valve and of parts of the breathing mask in a first position.

FIG. 1 shows schematically the construction of a breathing apparatus according to an embodiment of the invention. It has a compressed air source 2 with a compressed air source valve 4. Connected to the compressed air source valve 4 is an inlet 5 of a breathing regulator 6, which comprises a pressure reducer 7 and a lung-governed demand valve 8 (lung demand valve or LDV). A breathing mask 10 is connected by a first inlet connector 11 to an outlet 9 of the breathing regulator 6. A second air source 14 is either, as shown here, connected to a second inlet connector 12 of the breathing mask or connected to a connector with direct connection to the lung-governed demand valve. The second air source 14 can be, for example, a filter attached to the second inlet connector 12. In principle, it is also possible for the second inlet connector to be arranged on the breathing regulator. FIG. 1 shows schematically an apparatus wearer 13, who is wearing the breathing apparatus according to the invention and has fitted the breathing mask 10.

By means of a switching mechanism 20, 22 it is possible to switch between compressed air breathing from the compressed air source 2 via the lung-governed demand valve 8 or from the second air source 14. Finally, an exhalation valve 30 is present on the breathing mask, which exhalation valve is movable between a first and a second operating state, the opening pressure of the valve being higher in the second operating state and a higher internal pressure thus being effected in the breathing mask than in the first operating state. In the breathing apparatus according to the invention shown in FIG. 1, the switching mechanism is provided with an actuating member 20 on the lung-governed demand valve. The switching mechanism is so configured that, upon operation of the actuating member 20 for switching to compressed air breathing, the switching mechanism activates the lung-governed demand valve 8 and adjusts the exhalation valve 30 via the pressure adjusting mechanism 22 to the second operating state and, upon operation of the actuating member 20 for switching to breathing via the second air source 14, it deactivates the lung-governed demand valve 8 and adjusts the exhalation valve 30 to the first operating state.

Opposite the breathing apparatus according to the present invention as shown in FIG. 1, a breathing apparatus according to the prior art cited at the beginning is shown in FIG. 5. In the breathing apparatus in FIG. 5 according to the prior art, the compressed air source valve 4 forms the actuating member for the switching mechanism for switching between compressed air breathing from the compressed air source via the lung-governed demand valve or from the second air source. The compressed air source valve 4 also serves as the actuator for switching the exhalation valve 30 between the first and the second operating state and vice versa. In the breathing apparatus of FIG. 5, therefore, opening of the compressed air source valve 4 effects the supply of compressed air to the breathing regulator 6 and at the same time also the repositioning of the exhalation valve 30 by the communication line which is shown between the compressed air source valve 4 and the exhalation valve 30. This has the disadvantages described in the introduction to the description, which are linked with the fact that opening of the compressed air source valve 4, and thus the supply of compressed air to the breathing regulator 6, only takes place during use under possibly critical conditions.

By contrast, in the case of the breathing apparatus according to the invention as shown in FIG. 1, the compressed air source valve 4 can be opened before the apparatus is actually in use, when the apparatus wearer 13 has fitted the breathing apparatus. As a result, the breathing regulator 6 is supplied with compressed air before the apparatus is actually in use. Any fault in the supply of compressed air to the breathing regulator can therefore be detected even before the apparatus is actually in use. During this phase, the switching mechanism according to an embodiment of the invention ensures that the lung-governed demand valve remains deactivated, that is to say ultimately does not supply compressed air to the outlet of the breathing regulator 6. The actuating member of the switching mechanism is provided on the lung-governed demand valve or between the lung-governed demand valve and the pressure reducer which, when operated, ensures that the lung-governed demand valve is so activated that the compressed air supply already present in the breathing regulator 6 is conveyed via the lung-governed demand valve to the outlet 9 of the breathing regulator 6 and thus further to the first inlet connector 11 of the breathing mask. Simultaneously with this activation of the lung-governed demand valve, the switching mechanism acts upon the exhalation valve 30 via the pressure adjusting mechanism 22 in order to move the exhalation valve into the second operating state for compressed air breathing.

The pressure adjusting mechanism 22 can comprise, for example, a spring-loaded pneumatic valve. This spring-loaded pneumatic valve has a displaceable piston which at one end is connected mechanically to the exhalation valve in order to act thereon for switching between the two operating states. At the other end, the piston is exposed to the internal pressure of the breathing regulator. The piston is further acted upon by a spring tension which biases the piston into a position in which it holds the exhalation valve in the first operating state. After activation of the lung-governed demand valve by operation of the actuating member, the pressure rises, as a result of which an increased pneumatic force acts upon the piston and displaces the piston, against the spring bias, into a second position, this movement of the piston leading to a mechanical switching of the exhalation valve into its second operating state. When the pressure returns to normal, the piston is displaced again as a result of the spring bias, and this return movement of the piston causes the exhalation valve to be switched again into its first operating state.

Switching to compressed air breathing by simple manual operation of the actuating member 20 of the switching mechanism on the lung-governed demand valve is substantially easier for the apparatus wearer to carry out in a possibly critical use situation than in the prior art, because the lung-governed demand valve is within the field of vision of the apparatus wearer in front of the breathing mask and thus is readily accessible for operation. By contrast, in the prior art, the compressed air source valve had to be opened in this situation by rotation through several turns behind the back of the apparatus wearer, which means a substantially more complicated manual operation behind the back, out of the field of vision of the apparatus wearer.

Figure 3:
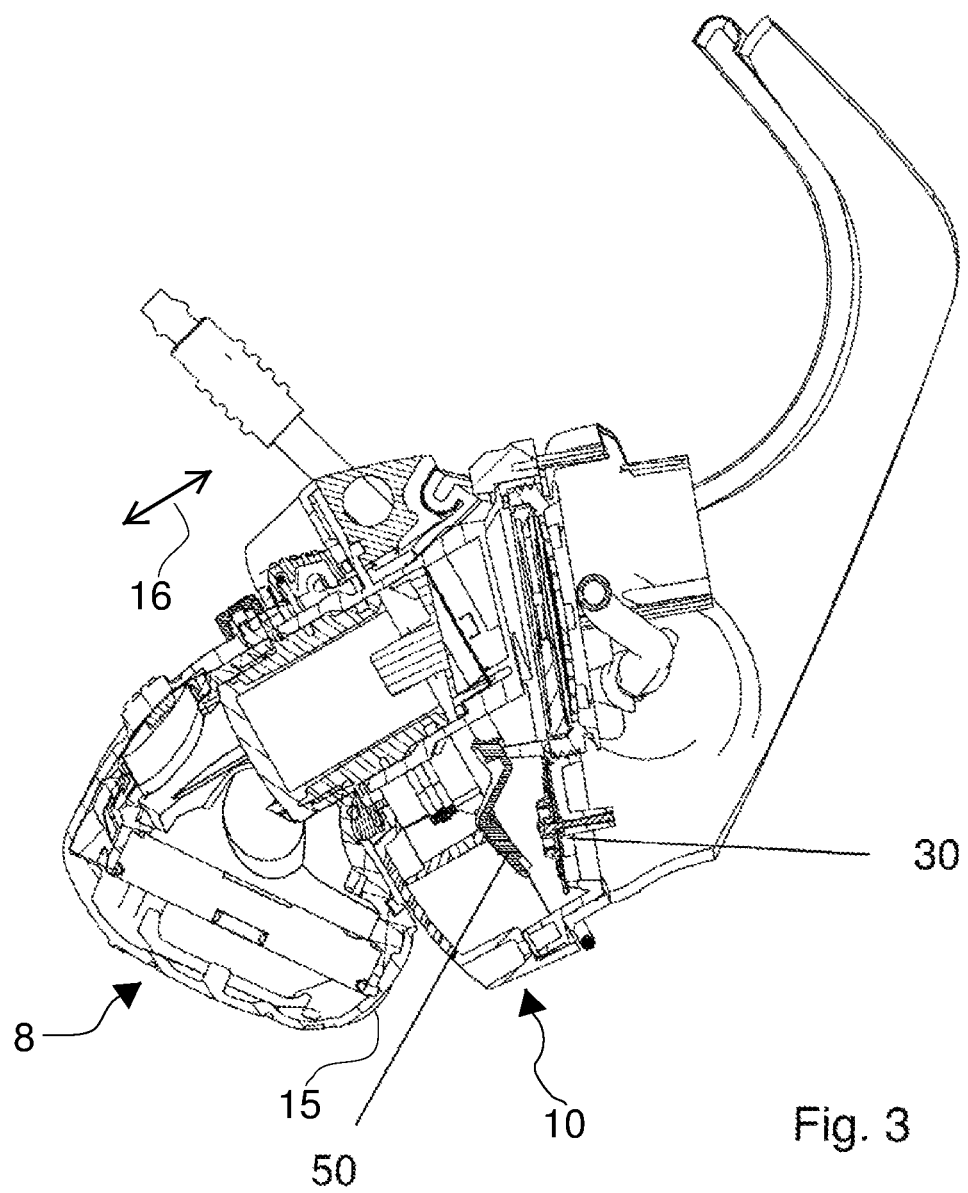
FIG. 3 is a sectional view of a lung-governed demand valve and of parts of the breathing mask in a second position.

FIG. 2 shows an embodiment of a switching mechanism on the lung-governed demand valve in a sectional view, the lung-governed demand valve 8 and parts of the breathing mask 10 being shown. In this embodiment, the housing 15 of the lung-governed demand valve 8 is mounted on the breathing mask 10 in a linearly displaceable manner along direction 16 and the linearly displaceable manner of the housing 15 acts as the actuating member of the switching mechanism. FIG. 2 shows the switching mechanism in a first position with the lung-governed demand valve 8 spaced from the breathing mask 10, and FIG. 3 shows the switching mechanism in a second position, in which the housing 15 of the lung-governed demand valve 8 has been displaced linearly into a second position closer to the breathing mask 10. The displacement path is indicated in FIG. 2 between the arrows a. A lever 50 is pivotably mounted inside the breathing mask 10. The lever 50 abuts a spring 52, which acts with its opposite end on the exhalation valve 30. FIG. 2 shows the first operating state of the exhalation valve 30, in which the pressure of the spring 52 on the exhalation valve 30 is low. If the apparatus wearer then operates the actuating member of the switching mechanism by pressing against the housing 15 of the lung-governed demand valve 8 in order to press it into the second position closer to the breathing mask 10, this displacement of the housing 15 acts mechanically upon the lever 50 so that it is pivoted into the position shown in FIG. 3 closer to the exhalation valve 30. As a result of this pivoting of the lever 50, the spring 52 (not shown in FIG. 3) is compressed and thus exerts a higher pressure on the exhalation valve 30. This increased pressure on the exhalation valve 30 increases its response pressure and thus effects switching into the second operating state.

At the same time, the displacement of the housing of the lung-governed demand valve causes the lung-governed demand valve to be activated, that is to say the lung-governed demand valve supplies compressed air at the outlet of the breathing regulator 6. For example, a pin which is fixed relative to the displaceable lung-governed demand valve can be provided, against which pin a valve of the lung-governed demand valve is pushed when the lung-governed demand valve is displaced, which valve is thereby opened and activates the lung-governed demand valve.

As a result of the activation of the lung-governed demand valve and the overpressure thereby established, a non-return valve at the second inlet connector is automatically closed. Other mechanisms can in principle also be used to close the second inlet connector by closing a valve, for example by acting mechanically on the valve, when changing over to compressed air breathing.

Figure 4:
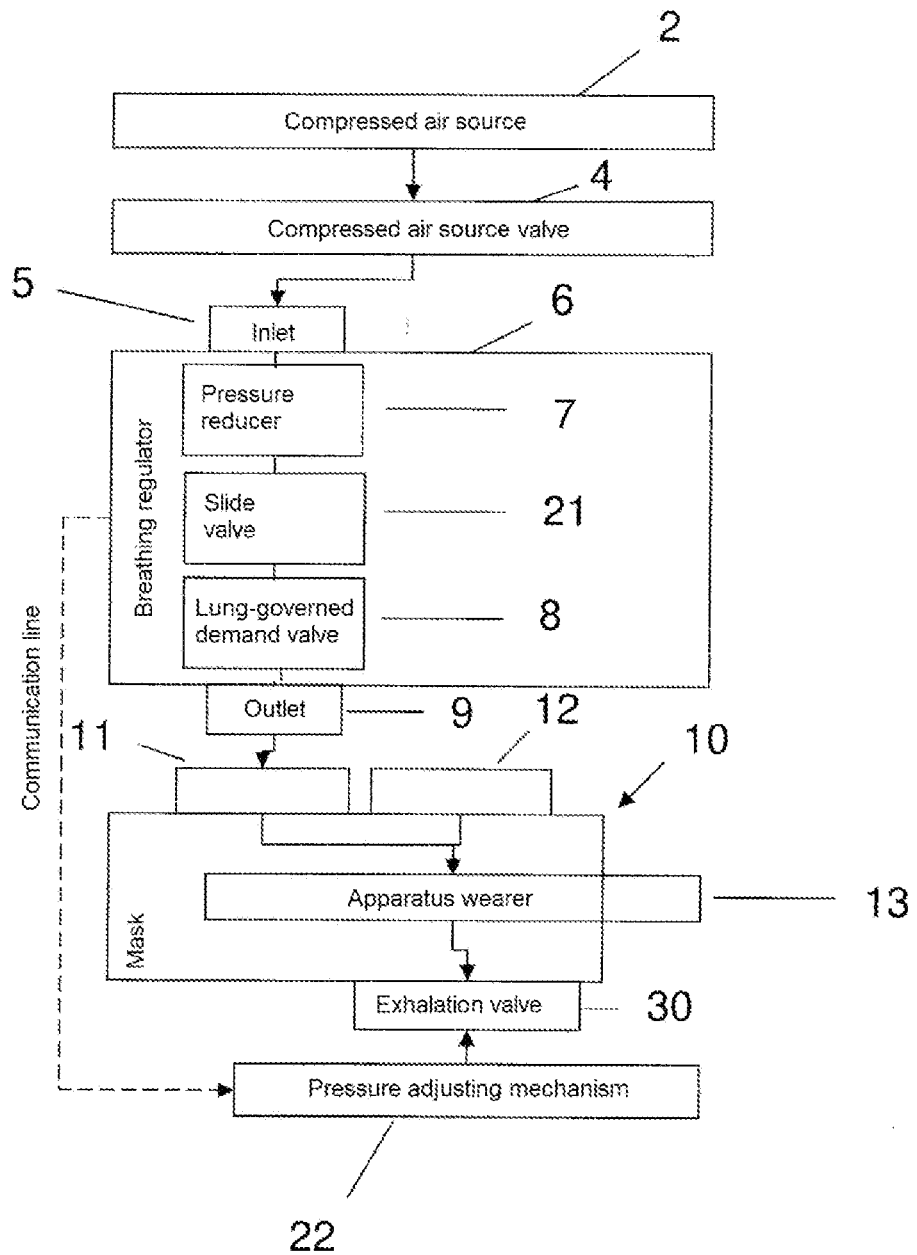
FIG. 4 is a schematic view showing the construction of a breathing apparatus according to the invention according to a further embodiment.

FIG. 4 shows the schematic construction of a further embodiment of a breathing apparatus. In this case, the switching mechanism has as the actuating member a slide valve 21, which is arranged in the breathing regulator between a pressure reducer and the lung-governed demand valve. By displacement of the slide valve 21, the flow of compressed air to the lung-governed demand valve is opened or closed. The switching mechanism further has a pressure adjusting mechanism 22 which is configured to record (respond to) the rise in pressure as a result of the opening of the compressed air flow to the lung-governed demand valve and then cause the exhalation valve 30 to be switched into the second operating state. Conversely, displacement of the slide valve 21 in the other direction causes the supply of compressed air to the lung-governed demand valve 8 to be interrupted, following which the sensor records (provides a response to) the resulting pressure drop of the compressed air flow to the lung-governed demand valve 8 and then the pressure adjusting mechanism 22 causes the exhalation valve 30 to be switched back into the first operating state.

While specific embodiments of the invention have been shown and described in detail to illustrate the application of the principles of the invention, it will be understood that the invention may be embodied otherwise without departing from such principles.

The invention claimed is:

1. A breathing apparatus comprising:
   a compressed air source with a compressed air source valve;
   a breathing regulator connected to the compressed air source valve, the breathing regulator comprising a pressure reducer and a lung-governed demand valve, the breathing regulator having an outlet;
   a breathing mask comprising a first inlet connector operatively connected to the lung-governed demand valve through the outlet of the breathing regulator, the breathing mask also comprising a second inlet connector;
   a second air source operatively connected either to the second inlet connector of the breathing mask or to a connector with direct connection to the lung-governed demand valve;
   a switching mechanism with an actuating member effecting switching between compressed air breathing from the compressed air source via the lung-governed demand valve and breathing from the second air source;
   an exhalation valve on the breathing mask, the exhalation valve being movable between a first and a second operating state, a higher internal pressure being effected in the breathing mask in the second operating state than in the first operating state, wherein:
   the actuating member of the switching mechanism is provided on the breathing regulator, the switching mechanism being so configured that, upon switching to compressed air breathing, the switching mechanism activates the lung-governed demand valve and adjusts the exhalation valve to the second operating state and, upon switching to breathing via the second air source, the switching mechanism deactivates the lung-governed demand valve to not supply compressed air to the outlet of the breathing regulator and adjusts the exhalation valve to the first operating state.

2. A breathing apparatus according to claim 1, wherein the actuating member is on the lung-governed demand valve and is configured to end valve blocking in the lung-governed demand valve when operated, and the switching mechanism comprises a pressure adjusting mechanism configured to record a rise in pressure as a result of the ending of valve blocking and to cause the exhalation valve to be switched into the second operating state upon recording the rise in pressure as the result of the ending of valve blocking.

3. A breathing apparatus according to claim 1, wherein the actuating member comprises a manually operated slide valve arranged in the breathing regulator between the pressure reducer and the lung-governed demand valve in order to open or close the flow of compressed air to the lung-governed demand valve by displacement of the slide valve, and a pressure adjusting mechanism configured to record the rise in pressure as a result of the opening of the compressed air flow to the lung-governed demand valve and cause the exhalation valve to be switched into the second operating state and to record the pressure drop as a result of the opening of the compressed air flow to the lung-governed demand valve and cause the exhalation valve to be switched into the first operating state.

4. A breathing apparatus according to claim 1, wherein a housing of the lung-governed demand valve is suspended on the breathing mask in a linearly displaceable manner between a first position and a second position relative to the breathing mask to cooperate with the switching mechanism, wherein displacement of the housing from the first position into the second position ends internal valve blocking in the lung-governed demand valve and switches the exhalation valve from the first operating state into the second operating state and, conversely, displacement from the second position into the first position effects valve blocking in the lung-governed demand valve and switches the exhalation valve from the second operating state into the first operating state.

5. A breathing apparatus according to claim 4, wherein the switching mechanism has a lever which acts upon the exhalation valve via a spring, the switching mechanism being configured to pivot the lever, upon displacement of the housing of the lung-governed demand valve from the first position into the second position, in such a manner that the pressure of the spring on the exhalation valve is increased and the exhalation valve is thereby moved into the second operating state, and, conversely, upon displacement of the housing of the lung-governed demand valve from the second position into the first position, to pivot the lever back so that the pressure of the spring on the exhalation valve is reduced and the exhalation valve is thereby moved into the first operating state.

6. A breathing unit comprising:
a breathing regulator connected to a compressed air source valve of a compressed air source the breathing regulator comprising a pressure reducer and a lung-governed demand valve the breathing regulator having an outlet;
a breathing mask comprising a first inlet connector operatively connected to the lung-governed demand valve through the outlet of the breathing regulator, the breathing mask also having a second inlet connector operatively connected to a second air source;
a switching mechanism having an actuating member, actuating a switching between compressed air breathing from the compressed air source via the lung-governed demand valve and breathing from the second air source; and
an exhalation valve on the breathing mask, the exhalation valve being movable between a first and a second operating state, a higher internal pressure being effected in the breathing mask in the second operating state than in the first operating state, wherein:
the actuating member of the switching mechanism is arranged on the breathing regulator, the switching mechanism being configured such that, upon switching to compressed air breathing, the switching mechanism activates the lung-governed demand valve and adjusts the exhalation valve to the second operating state and, upon switching to breathing via the second air source, the switching mechanism deactivates the lung-governed demand valve to not supply compressed air to the outlet of the breathing regulator and adjusts the exhalation valve to the first operating state.

7. A breathing apparatus comprising:
a breathing regulator with a compressed air source valve connection of a compressed air source, the breathing regulator comprising a pressure reducer and a lung-governed demand valve, the breathing regulator having an outlet;
a breathing mask comprising an inlet connector arrangement operatively connected to the lung-governed demand valve through the outlet of the breathing regulator, the breathing mask also being operatively connected to a second air source,
a switching mechanism switching between compressed air breathing from the compressed air source via the lung-governed demand valve and breathing from the second air source;
an exhalation valve on the breathing mask, the exhalation valve being movable between a first and a second operating state, a higher internal pressure being effected in the breathing mask in the second operating state than in the first operating state; and
a switching mechanism actuating member connected to the breathing regulator and actuating the switching mechanism wherein for switching to compressed air breathing the switching mechanism moves the exhalation valve to the second operating state and, for switching to breathing via the second air source, the switching mechanism deactivates the lung-governed demand valve to block flow of compressed air to the outlet of the breathing regulator and moves the exhalation valve to the first operating state.

8. A breathing apparatus according to claim 7, wherein:
the switching mechanism actuating member is connected to the lung-governed demand valve and switches off valve blocking in the lung-governed demand valve when actuated, and
the switching mechanism comprises a pressure adjusting mechanism responsive to a rise in pressure as a result of the switching off of valve blocking in the lung-governed demand valve to cause the exhalation valve to be switched into the second operating state.

9. A breathing apparatus according to claim 7, wherein:
the switching mechanism actuating member comprises a manually operated slide valve connected between the pressure reducer and the lung-governed demand valve in order to open or close the flow of compressed air to the lung-governed demand valve by displacement of the slide valve; and
the switching mechanism comprises a pressure adjusting mechanism;
the pressure adjusting mechanism responds to a rise in pressure, as a result of an opening of a compressed air flow to the lung-governed demand valve, by switching the exhalation valve to the second operating state; and
the pressure adjusting mechanism responds to a pressure drop, as a result of the opening of the compressed air flow to the lung-governed demand valve, by switching the exhalation valve to the first operating state.

10. A breathing apparatus according to claim 7, wherein:
the switching mechanism comprises a pressure adjusting mechanism configured to respond to pressure at the outlet of the breathing regulator, the pressure adjusting mechanism causing the exhalation valve to be switched into the second operating state upon recording a rise in pressure at the outlet of the breathing regulator.

11. A breathing apparatus according to claim 7, wherein:
the switching mechanism selectively opens and closes a flow of compressed air between the pressure reducer and the lung-governed demand valve.

12. A breathing apparatus according to claim 7, wherein:
the switching mechanism includes a pressure adjusting mechanism which is configured to respond to a rise in pressure as a result of opening of the flow of compressed air to the lung-governed demand valve and cause the exhalation valve to be switched into the second operating state.

13. A breathing apparatus according to claim 7, wherein:
a housing of the lung-governed demand valve is moveably mounted to the breathing mask to be linearly displaceable between a first position and a second position relative to the breathing mask, and cooperate with the switching mechanism;
displacement of the housing of the lung-governed demand from the first position into the second position switches off valve blocking in the lung-governed demand valve and switches the exhalation valve from the first operating state into the second operating state; and
displacement of the lung-governed demand from the second position into the first position switches on valve blocking in the lung-governed demand valve and switches the exhalation valve from the second operating state into the first operating state.

14. A breathing apparatus according to claim 13, wherein:
the lung-governed demand valve comprises a demand valve housing that is moveably mounted to the breathing mask to be linearly displaceable between the first position and the second position;
the switching mechanism comprises a spring and a lever acting on the exhalation valve via the spring;
the switching mechanism is configured to pivot the lever, upon displacement of the demand valve housing from the first position into the second position, whereby pressure of the spring on the exhalation valve is increased and the exhalation valve is thereby moved into the second operating state; and
the switching mechanism is configured to pivot the lever back, upon displacement of the demand valve housing from the second position into the first position, whereby the pressure of the spring on the exhalation valve is reduced and the exhalation valve is thereby moved into the first operating state.

15. A breathing apparatus according to claim 7, further comprising a compressed air source with a compressed air source valve connected to the compressed air source valve connection of the breathing regulator.

16. A breathing apparatus according to claim 15, wherein the inlet connector arrangement comprises a mask first inlet connector operatively connected to the lung-governed demand valve and a mask second inlet connector operatively connected to the second air source.

* * * * *